US011697800B2

(12) United States Patent
Wolff et al.

(10) Patent No.: US 11,697,800 B2
(45) Date of Patent: Jul. 11, 2023

(54) METHOD FOR THE SEPARATION OF VIRUS COMPOSITIONS INCLUDING DEPLETION AND PURIFICATION THEREOF

(71) Applicant: MAX-PLANCK-GESELLSCHAFT ZUR FÖRDERUNG DER WISSENSCHAFTEN E.V., Munich (DE)

(72) Inventors: Michael Wolff, Biederitz (DE); Michael Martin Pieler, Magdeburg (DE); Udo Reichl, Magdeburg (DE); Pavel Marichal-Gallardo, Magdeburg (DE)

(73) Assignee: MAX-PLANCK-GESELLSCHAFT ZUR FOERDERUNG DER WISSENSCHAFTEN E.V., Munich (DE)

(*) Notice: Subject to any disclaimer, the term of this patent is extended or adjusted under 35 U.S.C. 154(b) by 497 days.

(21) Appl. No.: 15/772,541

(22) PCT Filed: Sep. 26, 2016

(86) PCT No.: PCT/EP2016/072809
§ 371 (c)(1),
(2) Date: May 1, 2018

(87) PCT Pub. No.: WO2017/076553
PCT Pub. Date: May 11, 2017

(65) Prior Publication Data
US 2019/0085300 A1 Mar. 21, 2019

(30) Foreign Application Priority Data

Nov. 5, 2015 (EP) .................................... 15193102
Jun. 17, 2016 (EP) .................................... 16174958

(51) Int. Cl.
*C12N 7/00* (2006.01)
(52) U.S. Cl.
CPC ...... *C12N 7/00* (2013.01); *C12N 2760/16132* (2013.01); *C12N 2760/16151* (2013.01); *C12N 2760/16152* (2013.01)

(58) Field of Classification Search
None
See application file for complete search history.

(56) References Cited

U.S. PATENT DOCUMENTS 6,048,715 A 4/2000 Haynes et al.

FOREIGN PATENT DOCUMENTS

| EP | 2 412 817 A1 | 2/2012 |
|---|---|---|
| WO | 97/13841 A1 | 4/1997 |
| WO | 01/05949 A1 | 1/2001 |
| WO | 2012/134987 A1 | 10/2012 |
| WO | 2012/169970 A1 | 12/2012 |
| WO | 2013/180647 A1 | 12/2013 |

OTHER PUBLICATIONS

Wang et al., "Evaluation of steric exclusion chromatography on cryogel column for the separation of serum proteins", Journal of Chromatography, Elsevier Science Publishers B.V., NL, vol. 1333, Jan. 25, 2014, pp. 54-59.
Lee et al., "Principles and applications of steric exclusion chromatography", Journal of Chromatography A, vol. 1270, 2012, pp. 162-170.
Gagnon et al., Journal of Chromatography A 2014, 1324, 171-180.

*Primary Examiner* — Benjamin P Blumel
(74) *Attorney, Agent, or Firm* — WCF IP

(57) ABSTRACT

In a first aspect, the present invention relates to a method for the purification of virus compositions as well as biological macromolecular compounds in a sample comprising mixing the sample with osmolytes, like non-ionic organic polymers and contacting the mixed sample with a hydrophilic membrane, optionally washing the membrane, and eluting the virus preparations or biological macromolecular components from the membrane with an eluting solution containing reduced amounts or no osmolytes, like non-ionic organic polymer. Moreover, virus compositions and biological macromolecular components obtainable with the method according to the present invention are provided as well as the use of the method according to the present invention for purification of virus compositions including whole virus particles and virus-like particles or biological macromolecular components.

23 Claims, 1 Drawing Sheet

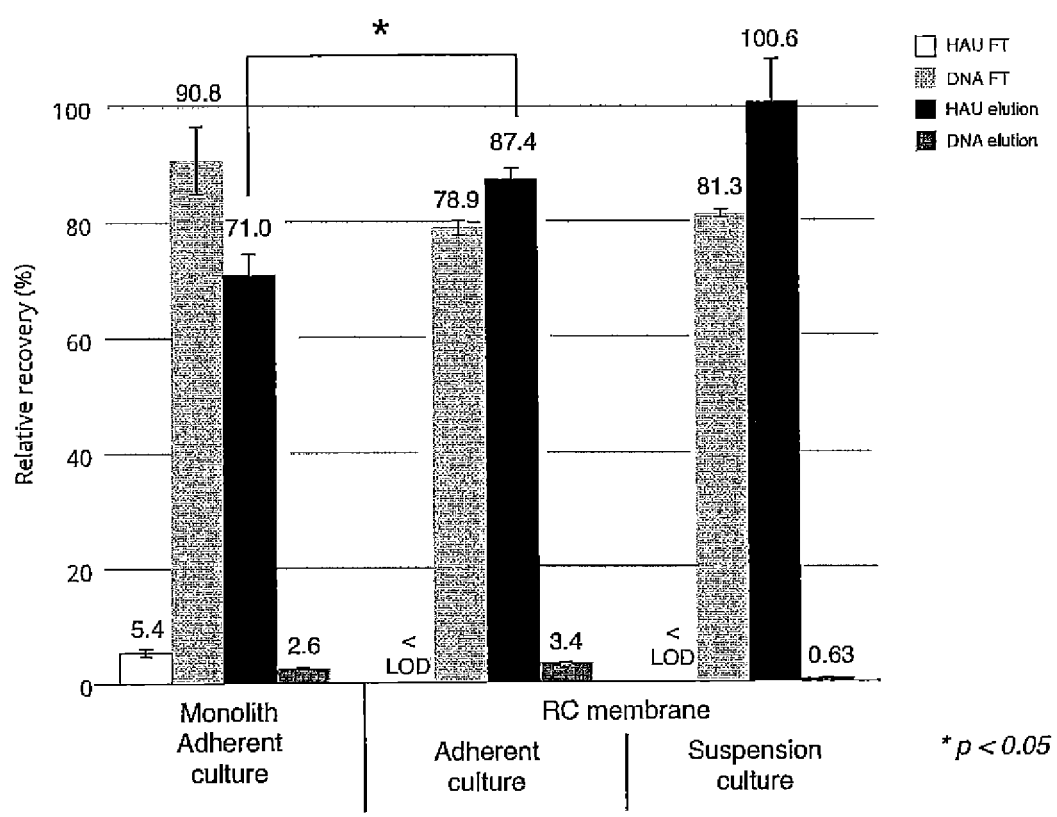

METHOD FOR THE SEPARATION OF VIRUS COMPOSITIONS INCLUDING DEPLETION AND PURIFICATION THEREOF

In a first aspect, the present invention relates to a method for the separation including depletion of virus compositions, as well as biological macromolecular components, in a sample comprising mixing the sample with osmolytes including non-ionic organic polymers and other suitable compounds including sugars and polyols and contacting the mixed sample with a hydrophilic membrane, optionally washing the membrane, and eluting the virus preparations or biological macromolecular components from the membrane with an eluting solution containing reduced amounts or no osmolytes including non-ionic organic polymer. In a further aspect, a method for the depletion of virus is provided. Moreover, virus compositions and biological macromolecular components obtainable with the method according to the present invention are provided as well as the use of the method according to the present invention for purification of virus compositions including whole virus particles and virus-like particles or biological macromolecular components. Finally, virus-depleted preparations including biopharmaceutical preparations are disclosed.

BACKGROUND ART

While on the one hand, isolation of whole virus particles, viral vectors, and virus-like particles (VLPs) as well as virus proteins, in the following referred to as virus, is of most importance for the production of vaccines useful in prophylactic or therapeutic vaccines against viral infections or for viral vectors used in gene therapy, on the other hand, it is also of importance to deplete viral contamination from biological products, like biopharmaceutical preparations. For example, the downstream processing of viruses obtained from natural resources, including egg- or cell culture-based production systems, is an elaborate process that requires careful design consideration. Virus-like particles resemble viruses, but are non-infectious because they do not contain any viral genetic material. The expression of viral structural proteins, such as envelope or capsule proteins, can result in the self-assembly of virus-like particles. Viruses as viral vectors are also in the focus of gene therapy.

The degree of complexity for downstream processing of viruses is related to the product source to be purified including the initial volume, product concentration, concentration and heterogeneity of impurities as well as the product itself including its physiochemical characteristics, stability, the final amount required, and the form to be provided.

Various methods has been described for enabling downstream processing for obtaining purified virus material. For example, EP 2 144 937 B1 describes a method for purification of virus and viral proteins based on sulfated cellulose membranes.

Size exclusion chromatography (SEC) requires column packing and represents a cost extensive, laborious method for purification of virus compositions. Other methods are described in the art, including ion-exchange chromatography based on the use of monoliths.

In U.S. Pat. No. 6,048,715 A1 and WO 2012/169970 A1 the purification of biological products by constrained cohydration chromatography is described.

Furthermore, in WO 2012/169970 processes are described for the purification of biological products by constrained co-hydration chromatography (steric-exclusion chromatography). The method described therein generally refers to the purification of hydrated target species including purification of biological materials such as antibodies, viruses, cells and cellular organelles in connection with chromatography matrices. However, this document is silent on depletion of virus from samples including biopharmaceutical preparations.

Recently, Gagnon P. et al, Journal of Chromatography A 2014, 1324, 171-180 described a high productivity purification of immunoglobulin G monoclonal antibodies on starch coated magnetic nanoparticles by steric exclusion with polyethylene glycol as an alternative for packed chromatography columns. However, the publication does not refer to viral load of said samples.

Despite the advantages monoliths offer, the use of monoliths is expensive when compared to membrane adsorbers, at least for vaccine manufacture. Thus, the costs of the monoliths challenge their single use application. Hence, they require cleaning validation and the risk of process inconsistency due to fouling.

In addition, complex means are required for effecting traditional size exclusion chromatography as well as constrained co-hydration chromatography via monoliths. That is, major drawbacks of applying column chromatography include long process time with large recovery liquid volume as well as laborious and complex process steps.

Therefore, it is an object of the present invention to provide a method for purification of virus compositions as well as biological macromolecular components in a simple manner overcoming the drawbacks in the art. Another object is the provision of methods for depletion of virus from samples including biopharmaceutical preparations.

It is another object of the present invention to provide virus compositions, in particular, virus particles and virus like particles with high purity as well as biological macromolecular components. Further, another object of the present invention is to provide virus-depleted samples including virus-depleted pharmaceutical compositions.

SUMMARY OF THE PRESENT INVENTION

In a first aspect, the present invention relates to a method for the purification of virus compositions and/or biological macromolecular components in a sample comprising steps of:
- mixing the sample containing virus compositions and/or biological macromolecular components with an osmolyte like a non-ionic organic polymer;
- contacting the mixture of the sample containing virus composition and/or biological macromolecular components and the osmolyte, like the non-ionic organic polymer, with a hydrophilic membrane;
- optionally washing the hydrophilic membrane with a washing solution containing an osmolyte, like a non-ionic organic polymer; and
- eluting the virus composition and/or biological macromolecular components from the membrane with an elution solution containing a reduced concentration compared to the concentration present in the sample or no osmolyte, like a non-ionic organic polymer, for obtaining purified virus compositions and/or biological macromolecular components.

Of note, the term "purification" or the term "depletion" includes the embodiment of separation.

Particularly preferred, the hydrophilic membrane is a cellulose membrane, like regenerated cellulose or a reinforced cellulose membrane, while in another embodiment, the non-ionic organic polymer is an aliphatic polyether like polyalkylene glycol, in particular a polyethylene glycol, or polypropylene glycol, or a poloxamer.

In another aspect, the present invention relates to the virus compositions and/or biological macromolecular components obtainable with the method according to the present invention. In a preferred embodiment, the virus composition is a purified virus composition of either whole virus particles or virus like particles.

In another aspect, the present invention provides the use of the method according to the present invention for isolating virus compositions and/or biological macromolecular components. Finally, the present invention provides the use of a kit for purification of virus particles and/or virus like particles as well as biological macromolecular components including osmolytes like non-ionic organic polymers as defined herein as well as a hydrophilic membrane. The kit is preferably designed for single use.

In addition, the present invention relates to a method for depleting virus from samples, like from pharmaceutical preparations, comprising the steps of
mixing a sample containing virus with an osmolyte, like a non-ionic organic polymer;
contacting the sample containing virus and osmolyte, like a non-ionic organic polymer, with a hydrophilic membrane allowing adherence of said virus to said hydrophilic membrane;
collecting the flow-through or the solution separated from the hydrophilic membrane;
optionally, repeating the contact and collecting steps;
for obtaining virus depleted samples, like virus depleted biopharmaceutical preparations.

In another aspect, the present invention provides virus-depleted samples including biopharmaceutical preparations obtainable with the method according to the present invention. Finally, the present invention provides the use of a kit for virus depletion including osmolyte, like non-ionic organic polymer according to the present invention and a hydrophilic membrane according to the present invention, in particular, suitable for single use.

BRIEF DESCRIPTION OF THE DRAWINGS

FIG. 1 shows the results of the purification of MDCK cell culture-based influenza virus particles with hydroxyl (OH) monoliths and regenerated cellulose membranes. The different purifications were performed at the same experimental conditions, i.e. binding buffer and elution buffer. The best performance was achieved for MDCK suspension cell culture-derived influenza virus particles using regenerated cellulose membranes with no detectable hemagglutination activity (aHA) losses, expressed as hemagglutination units (HAU) in the collected product fraction with a DNA clearance higher than 99%. Relative recoveries and standard error of hemagglutination units (HAU) and DNA from the purification of adherent ($MDCK_{adh}$) and suspension ($MDCK_{sus}$) cell culture-based influenza virus particles. FT=flowthrough, RC=regenerated cellulose.

DETAILED DESCRIPTION OF THE PRESENT INVENTION

In a first embodiment, the present invention relates to a method for the purification and/or separation of virus compositions and/or biological macromolecular components from a sample comprising the steps of mixing the sample containing virus compositions and/or biological macromolecular components with an osmolyte, like a non-ionic organic polymer;
contacting the mixture of the sample containing virus composition and/or biological macromolecular components and osmolyte, like non-ionic organic polymer, with a hydrophilic membrane;
optionally washing the hydrophilic membrane with a washing solution containing an osmolyte, like a non-ionic organic polymer; and
eluting the virus composition and/or biological macromolecular components from the membrane with an elution solution containing a reduced amount of the osmolyte, like the non-ionic organic polymer compared to the amount present in the sample or no osmolyte, like non-ionic organic polymer for obtaining purified virus compositions and/or biological macromolecular components.

That is, the present inventors recognized that by simply adding the osmolyte, like the non-ionic polymer, in a pre-determined amount to the sample containing virus compositions and/or biological macromolecular components and, after mixing the sample containing the virus composition and/or biological macromolecular components with the osmolyte, like the non-ionic organic polymer, applying the same to the hydrophilic membrane, allows a fast and reliable isolation and/or separation of the desired virus composition and/or biological macromolecular components, e.g. whole virus particles and virus-like particles, from a material containing the same. That is, the method according to the present invention allows highly effective purification of whole virus particles, viral vectors and virus-like particles whereby the compounds required for conducting the method, namely, the osmolytes, like the non-ionic organic polymer and the hydrophilic membranes, are easily commercially available and, in addition are inexpensive; in particular, compared to the methods based on monolith chromatography.

In another embodiment, the present invention is a method for virus depletion from samples, like from pharmaceutical compositions, comprising the steps of
mixing a sample containing virus with an osmolyte, like a non-ionic organic polymer;
contacting the sample containing virus and a osmolyte, like non-ionic organic polymer, with a hydrophilic membrane allowing adherence of said virus to said hydrophilic membrane;
collecting the flow-through or the solution separated from the hydrophilic membrane;
optionally, repeating the contact and collecting steps;
for obtaining virus depleted samples, like virus depleted biopharmaceutical preparations.

The method is a cheap and fast as well as a reliable method for virus depletion.

Using a method according to the present invention achieved high product recoveries while reducing the level of contaminants. Further, the time for effecting the method is reduced compared to the time required for effecting the laborious method including SEC or other column based methods described in the art. Hence, the productivity can be significantly enhanced due to the easiness of the method according to the present invention. That is, on the one hand it is possible to purify the virus compositions and/or biological macromolecular components from samples while on the other hand, it is possible to allow virus depletion from samples containing molecules of interest, in particular, biopharmaceutical preparations to be administered to subjects in need thereof including human, e.g. depletion from cell culture in microbial or cell-based production processes.

As used herein, the term "virus" refers to whole virus also identified as virus particles and viral vector as well as virus like particles (VLPs) and viral proteins unless otherwise identified.

The term "biological macromolecular components" refers to biological macromolecules containing amino acid residues. The biological macromolecular components may be a single molecule, like a single protein, or may be macromolecular complexes, e.g. complexes of several subunits of a protein or different types of proteins. For example, the biological macromolecular components are molecules or complexes of at least 60 kDa size, e.g. at least 100 kDa size, like at least 150 kDa size. Examples of these components include immunoglobulins, enzymes, etc. Typically, the purification results in a separation of compounds with higher molecular weight and lower molecular weight.

The term "depletion" or "virus depletion" refers to the reduction of the amount of virus in a sample. Typically, the reduction is a reduction compared to the amount of virus in the starting sample expressed as logarithmic reduction value (log 10) of at least 1, e.g. of at least 2, like at least 3, e.g. at least 4, like at least 5. For example the reduction is a reduction compared to the amount of virus in the starting sample of at least 50%, e.g. at least 70%, like at least 80%, e.g. at least 90%, like at least 95%. In an embodiment, the term depletion refers to embodiments wherein with conventional methods no virus can be detected. For example depletion means logarithmic reduction value (log 10) of at least 1-2.

The term "osmolyte" refers to a compound affecting osmosis. These compounds include sugars, like mono- or disaccharides including glucose, sucrose and trehalose; polyols, like glycerol or sorbitol; as well as suitable amino acids.

In comparison to SEC, no column packing needs to be performed and the productivity is much higher due to the higher flow rates achievable. The size of the required chromatography matrix is much smaller and the amount of sample that can be loaded onto the hydrophilic membrane is determined only by the capacity for the total virus compounds and/or biological macromolecular components.

Further, the separation step according to the present invention may be repeated with different amounts or different types of osmolyte, line non-ionic polymer. Thus, it is possible to successively separate compounds of a desired size. For example, starting with a non-ionic polymer of large size, like PEG-6000, or at low concentration, large compounds may be adsorbed to the hydrophilic membrane while in a subsequent step using higher concentration of the said PEG-6000, or a lower sized PEG compound with the same concentration would allow to separate another fraction of virus or macromolecular compounds. For example, it is submitted that using PEG-6000 with 10% results in the separation of similar compounds as using PEG-10000 with 2% or PEG-600 with 20%.

Not to be bound to theory, PEG-6000 in the range of 10-12% allow virus depletion of virus in size of amount 25 nm or lower. That is, even smallest virus can be depleted. In contrast, IgG remain in the flow through allowing virus depletion of these important biopharmaceuticals.

In comparison to affinity matrices, either bead-based or membrane-based, the method according to the present invention is not limited by the availability of the affinity ligands. Affinity ligands can also be expensive to manufacture or to couple to an existing membrane. This is a reason for increasing production costs and hinders the possibility of using such a material for single use.

In ion exchange chromatography, product stability could be compromised by high concentrations of salt, and the virus product can be recovered in a particular buffer composition only.

Constrained co-hydration chromatography or steric exclusion chromatography based on monoliths work also with a size-based principle. However, although monoliths may have some advantages compared to bead based resins (e.g. high binding capacity, convective flow) they remain expensive, at least for vaccine manufacture. Hence, monoliths are preferentially not used for single use applications due to the high costs. Moreover, for multiple applications they require cleaning validation and the risk of process inconsistency due to impurity carryover.

A main advantage of the method according to the present invention are the low costs and high safety of the osmolyte, like the non-ionic polymer and the membranes used, the high speed and productivity, and the potential of using it as a platform approach for any kind of virus compositions as well as biological macromolecular components, in particular, any kind of virus particles and VLPs since the separation is mainly based on size. Moreover, due to the easiness, and, in addition, due to the inexpensive material, the process can be adapted to be for single-use, thus, eliminating the need for cleaning validation, the risk of impurity carryover and product cross-contamination.

That is, the hydrophilic membranes are low cost hydrophilic membranes, e.g. the membranes are cellulose membranes, like regenerated cellulose membranes or reinforced membranes. In an embodiment, the hydrophilic membrane is a simple regenerated cellulose membrane being low in costs and easily available as well as easily commercially processable.

Regarding the hydrophilic membrane, it is preferred that the hydrophilic membrane is a membrane having micron-sized pores. That is, for example in case of cellulose the pore size of said cellulose is at least 100 nm, like at least 200 nm, e.g. at least 0.4 µm. For example, the range is of from 0.1 to 20 µm. The nano-sized filters used so far are in the range of from 15-50 nm, like 15-20 nm. Suitable pore sizes are e.g. 0.1, 0.2, 0.4, 0.65, 0.8, 1.0 µm as described for cellulose or cellulose derivatives.

In another embodiment, the virus composition is a whole virus particle or is a composition of virus like particles (VLPs) or is a mixture of two or more different whole viruses, or is a mixture of a whole virus particles and a virus like particle. The composition may be a composition of virus proteins and non-virus proteins. In an embodiment, the method for the purification is used for purifying virus particles or VLPs for later use in vaccines or other medical applications. The virus particles, VLPs, or macromolecules may be influenza virus, or yellow fever virus, or human papilloma virus, or vaccinia virus, or adenovirus, or adeno-associated virus, or baculovirus, or hepatitis virus, or lentivirus, or poliovirus, or rabies virus, or rotavirus, or rubella virus, or zika virus, particles or fragments thereof. In addition, the virus composition is a composition of viral vectors, e.g. useful in gene therapy or in vaccination.

In case of virus depletion and/or virus separation, the sample is a sample containing components or molecules for later administration to individuals including humans. Thus, these preparations suitable for administration to individuals should be void of viral components limiting the risk of viral infection accordingly. Today cell-lines used for the production of therapeutics bear the risk of viral contamination caused from themselves or with constituents of the cell culture media. The risk of viral contamination requires critical consideration. Viral infection cannot be removed from the cell-lines with chemicals and there are no preservatives with viricidal activity that can be included in the final product. Therefore, viral contamination must be reduced to an acceptable level during downstream processing of the preparation. For example, in case of monoclonal antibody manufacturing, the most dedicated operations for clearance are low pH inactivation and virus filtration, the latter being performed at the end of the downstream processing with pore sizes as small as 20 nm.

However, this prior art method requires laborious work. In contrast, the method according to the present invention representing a so called hydrodynamic retention chromatography (HRC) makes use of low cost membrane adsorbers with micron-sized pores for the depletion of the virus including virus particles from the preparations, thus, providing virus depleted biopharmaceutical preparations accordingly.

Unlike traditional viral filtration, the mechanical integrity of the membrane and the HRC does not compromise virus clearance performance. With HRC, selectivity can be tweaked by the user, as opposed to conventional virus filters where selectivity is determined by the pore size. In view of the low costs of the membranes, single use operation is possible. In contrast to nano-sized viral filtration, the pore sizes of the membrane according to the present invention allows high flow rates, lowering the risk for product loss due to filtration effects. Hence, HRC has the potential for higher productivity. Additionally, using HRC the depleted virus can be enriched and recovered for analytics.

The non-ionic organic polymer may be a non-ionic surfactant or non-ionic organic polymer having a hydrophobic part and a hydrophilic part.

In another embodiment, the osmolyte, namely, the non-ionic organic polymer is a polyol. That is, a polyol is a polyalcoholic compound containing hydroxylic groups, like an aliphatic polyether. Polyols may be linear or may be cyclic. In an embodiment, the polyols are oligo- or polymeric polyols based on short-chain alcohols. Examples of polyols are polyalkylene glycols or oligomeric glycerin. In an embodiment, the polyol is a polyethylene glycol or polypropylene glycol or mixtures thereof having an average molecular mass (also known as average molecular weight) of 100 to 100000 g/mol, for example, the polyethylene glycol or polypropylene glycol is a compound having an average molecular mass of 600 to 10000 g/mol.

In another embodiment, the non-ionic organic compound is a polyethylene glycol of PEG-600 to PEG-10000 including PEG 6000.

In another embodiment, the concentration of the osmolyte, like the non-ionic organic compound, for example in form of polyalkylene glycol including polyethylene glycol and polypropylene glycol in the sample contacted with the hydrophilic membrane is in the range of from 0.1 to 40 weight-%, e.g. 1 to 20 weight-%, like 2 to 10 weight-% based on the weight of the total sample.

That is, mixing the sample containing the virus composition and/or biological macromolecular components, in particular, containing the virus particles or VLPs, with the osmolyte, in form of a non-ionic organic polymer, e.g. being selected from polyethylene glycol or polypropylene glycol or mixtures thereof, allows to efficiently purify the virus composition and/or biological macromolecular components with low costs and preferably without any further laborious cleaning steps. Since elution of the purified virus composition and/or biological macromolecular components is effective with a buffer containing a lower concentration or no osmolyte, like non-ionic organic polymer, it may not be necessary to effect further process steps for eliminating the same from the sample. Further, the method allows for an easy and cheap method for virus depletion and/or separation.

Moreover, in an aspect of the present invention, the amount and size of the non-ionic organic polymer in form of the polyol, in particular, in form of the polyalkylene glycol, like polyethylene glycol or polypropylene glycol or mixtures thereof, depend primarily on the size and the shape of the virus particles or VLP to be purified. In this connection, it is preferred that in case of larger virus or larger VLP, smaller polyalkylene glycol (PAG), i.e. PAG, like PEG, with low average molecular mass, will be used, like PEG-600 to PEG-4000 while in case of smaller virus or VLPs, polyalkylene glycol with higher average molecular mass will be used.

Alternatively, the non-ionic organic polymer is a poloxamer.

Moreover, in case of larger virus or VLP, the concentration of the polyalkylene glycol, like the polyethylene glycol or polypropylene glycol or mixtures thereof is lower, e.g. in the range of from 1 to 10% (w/w) while with smaller virus or smaller VLP, the concentration of the polyalkylene glycol is higher.

Typically, 1 to 20 weight-%, like 2 to 12% (w/w) polyalkylene glycol, for example in form of polyethylene glycol, is added to the sample containing the virus composition. In case of biological macromolecular components, the amount of polymer added is in between 1 to 40% (w/w) like 2 to 20% (w/w).

Applying the method according to the present invention, it is possible to efficiently reduce the amount of contaminants in the sample, e.g. the amount of contaminating DNA. In an embodiment, the amount of DNA in the purified sample compared to the amount of DNA in the starting sample is reduced at least 50%, e.g. at least 70%, like at least 80%, e.g. at least 90%, at least 95%.

That is, typically, the contaminants including DNA and host cell proteins are present in the effluent and the washing buffer while the virus remains in or on the hydrophilic membrane. These viruses present in or on the hydrophilic membranes may be eluted with an elution buffer not containing any osmolyte, like non-ionic organic polymer or containing a reduced amount of the osmolyte, like non-ionic organic polymer compared to the sample or the washing buffer. In addition, the eluted virus compositions do not contain large amounts of osmolyte, like non-ionic organic polymers, thus, reducing further steps accordingly.

Further, the virus-depleted preparation obtained after conducting the method according to the present invention for virus depletion is a preparation wherein the viral load is substantially reduced. For example, the viral load in the purified sample compared to the viral load in the starting sample expressed as logarithmic reduction value (log 10) of at least 1, e.g. of at least 2, like at least 3, e.g. at least 4, like at least 5. For example, the reduction is a reduction of virus in the virus depleted sample compared to the amount of virus in the starting sample is reduced at least 50%, e.g. at least 70%, like at least 80%, e.g. at least 90% like at least 95%. That is, typically the contaminating virus are bound to the hydrophilic membrane while the active components, like the monoclonal antibody or other biopharmaceuticals are in the effluent. Thus, it is possible to deplete virus and, optionally, other undesired biological macromolecular molecules simply by adsorption to the hydrophilic membrane. The virus depleted preparations may undergo further steps in the downstream processing. These further steps include washing of the preparation to eliminate the osmolyte, like the non-ionic organic polymer as well as re-purification with the same HRC method to capture the virus depleted product, e.g. by changing the osmolyte, as well as further purification of the desired compounds including biopharmaceuticals.

That is, according to the present invention either the method for purification of method for virus or virus depletion may be part of a chain of methods for downstream processing of a sample obtained e.g. from cell culture or other sources.

In this connection, the skilled person can easily determine the most suitable osmolyte, like non-ionic organic polymer for either virus purification or virus depletion.

Further, the present invention relates to the use of the method according to the present invention for isolating viruses or VLPs, in particular, vaccinia virus and influenza virus containing compositions for use in vaccines.

Other examples for suitable virus include: yellow fever, dengue virus, Zika virus, Chikungunya virus, polio virus, human papilloma virus, adenovirus, adeno-associated virus, baculovirus, flavivirus, hepatitis virus, herpes simplex virus, japanese encephalitis virus, lentivirus, measles virus, mumps virus, poliovirus, rabies virus, rotavirus, rubella virus, Semliki forest virus, and where applicable VLPs of the corresponding viruses like human papilloma virus VLPs and influenza VLPs.

The present invention relates in addition to the use of the method according to the present invention for virus depletion and/or separation from samples including biological preparations like biopharmaceutical preparations.

Further, the present invention relates to the use of a kit for purification of viruses and/or VLPs. The kit contains osmolytes, like non-ionic organic polymers as defined herein as well as a hydrophilic membrane. The kit is useful for single use only due to the low costs of the material. Thus, laborious cleaning of the equipment is not necessary.

Finally, the present invention relates to the use of a kit for the depletion of virus including virus particles and/or VLPs. The kit contains osmolytes, like non-ionic organic polymers as defined herein as well as a hydrophilic membrane. The kit is useful for single use due to the low costs of the material. Thus, laborious cleaning of the equipment is not necessary and the use of the kit can be incorporated easily in a downstream process.

The following examples illustrate the invention further without limiting the same to the specific embodiment described in the examples.

EXAMPLES

Example 1

Purification of Adherent MDCK ($MDCK_{adh}$) Cell Culture-Based Influenza Virus Particles Clarified cell culture fluid (cCCF) containing influenza virus particles produced in adherent MDCK cells was used as starting material. Two different adsorption matrices were used: 1) a 0.34 mL monolith with hydroxyl (OH) ligands and 2) 75 $cm^2$ of regenerated cellulose (RC) membranes with a pore size of 1 µm and a diameter of 2.5 cm. The membranes were stacked inside a stainless steel filter holder. All experiments were performed on a Akta liquid chromatography system (GE Healthcare Life Sciences, Uppsala, Sweden). Triplicate runs were performed for both adsorption matrices. The purification runs were conducted as follows: the matrix was equilibrated with binding buffer (phosphate buffer saline (PBS)) at a concentration of 8% PEG 6000. A volume of 8 mL of starting material was diluted 1:2 with a 16% (w/w) PEG 6000 stock solution to achieve a final PEG concentration of 8% (w/w) in the sample equal to that of the binding buffer; this mixture is defined as injected sample. After sample injection, the matrix was washed with binding buffer until stable UV absorbance was achieved. Desorption of influenza virus particles was carried out by flushing the matrix with PBS without PEG 6000. The hemagglutination activity (aHA) expressed as hemagglutination units (HAU) and DNA content were quantified in the injected sample, the flow through fraction and the collected product fraction. The results showed that at the same process conditions, about 5% of influenza virus is lost in the flow through when using the monolithic matrix. In the case of the RC membrane, HAU in the flow through was below the level of detection (LOD). The HAU recovery was about 71% and 87% for the monolith and RC membranes, respectively; this difference was found to be statistically significant with $p<0.05$.

Example 2

Purification of Suspension MDCK ($MDCK_{sus}$) Cell Culture-Based Influenza Virus Particles The conditions of example 1 were repeated in RC membranes with cCCF containing influenza virus particles produced in suspension MDCK cells. HAU was below LOD in the flowthrough (FT). The HAU recovery was 101%.

The data obtained are shown in the table below and FIG. 1.

TABLE 1

Relative recoveries and standard error of hemagglutination units (HAU) and DNA from purification of adherent ($MDCK_{adh}$) and suspension ($MDCK_{sus}$) cell culture-based influenza virus particles.

| Matrix/sample | HAU (%) FT | HAU (%) Elution | DNA (%) FT | DNA (%) Elution |
|---|---|---|---|---|
| Monolith/$MDCK_{adh}$ | 5.39 ± 0.71 | 71.03 ± 3.61 | 90.77 ± 5.84 | 2.57 ± 0.16 |
| RC membrane/$MDCK_{adh}$ | <LOD | 87.38 ± 1.83 | 78.89 ± 1.25 | 3.45 ± 0.08 |
| RC membrane/$MDCK_{sus}$ | <LOD | 100.56 ± 7.33 | 81.25 ± 0.68 | 0.63 ± 0.00 |

HAU = hemagglutination units, FT = flowthrough, RC = regenerated cellulose, LOD = limit of detection In addition, as demonstrated, the HAU is below LOD in the flowthrough (FT), thus, demonstrating that virus depletion is efficient with the method according to the present invention. In contrast, the monolith matrix corresponding to the method described in WO 2012/169970 is not as efficient accordingly.

Further, in table 2, a list of successfully purified viruses according to the method of the present invention is shown.

TABLE 2

Purified virus based on the method according to the present invention

| Virus | Family (Genus) | Size (nm) | Virion Morphology | Envelope | Genome |
|---|---|---|---|---|---|
| Adeno-associated virus | Parvoviridae | 20-25 | icosahedral | no | ssDNA |
| Influenza A virus | Orthomyxoviridae | 80-120 | pleomorphic, spherical | yes | (−)ssRNA |
| Lentivirus | Retroviridae | 80-130 | spherical | yes | (+)ssRNA |
| Measles virus | Paramyxoviridae | 120-270 | pleomorphic | yes | (−)ssRNA |
| Vaccinia virus | Poxviridae | 250-270-360 | brick-shaped | yes | dsDNA |
| Yellow fever virus | Flavivirus | 40-50 | icosahedral | yes | (+)ssRNA |

The invention claimed is:

1. A method for the purification and/or separation of virus compositions and/or biological macromolecular components in a sample
comprising the steps of
mixing the sample containing virus compositions and/or biological
macromolecular components with an osmolyte, wherein the osmolyte is a non-ionic organic polymer;
contacting the mixture of the sample containing virus composition and/or biological macromolecular components and the osmolyte with a cellulose membrane having pores with a pore size of at least 0.4 μm;
optionally washing the cellulose membrane with a washing solution containing the osmolyte; and
eluting the virus composition and/or biological macromolecular components from the cellulose membrane with an elution solution containing no or a reduced amount of the osmolyte for obtaining purified virus compositions and/or biological macromolecular components.

2. A method for virus depletion from samples, comprising the steps of
mixing a sample containing virus with an osmolyte, wherein the osmolyte is a non-ionic organic polymer;
contacting the sample containing virus and the osmolyte with a cellulose membrane having pores with a pore size of at least 0.4 μm and allowing adherence of said virus to said cellulose membrane;
collecting a flow-through or a solution separated from the cellulose membrane;
optionally, repeating the contact and collecting steps;
whereby virus depleted samples are obtained.

3. The method according to claim 1 wherein the virus compositions contain whole virus particles or virus like particles (VLPs) or viral gene vectors.

4. The method according to claim 1 wherein the osmolyte is a polyol or poloxamer.

5. The method according to claim 1 wherein the osmolyte is a polyalkylene glycol.

6. The method according to claim 1 wherein the virus composition is or includes virus particles or virus like particles (VLP), and wherein the osmolyte is polyethylene glycol, whereby an amount and size of the polyethylene glycol mixed in said mixing step is dependent on a size of the virus particles or the VLP to be purified.

7. The method according to claim 1 further comprising purifying different viruses or virus and particles from the same sample based on an amount and a size of the osmolyte mixed in said mixing step.

8. The method according to claim 1 wherein the osmolyte is a polyethylene glycol of PEG-600 to PEG-10000 and/or the PEG-concentration in the sample contacted with the cellulose membrane is in the range of from 0.1 to 40% (w/w) based on the sample.

9. The method according to claim 1 wherein the virus composition obtained is reduced in the amount of DNA compared to the starting sample of at least 50%.

10. The method according to claim 2 wherein an amount of virus in the sample is reduced by an amount of at least 50% compared to the starting sample.

11. The method according to claim 1 wherein the sample contains virus compositions including whole virus and/or VLP of one or more of vaccinia virus and influenza virus.

12. The method according to claim 2 wherein the virus includes whole virus particles or virus like particles (VLPs) or viral gene vectors.

13. The method according to claim 2 wherein said cellulose membrane is a regenerated cellulose membrane or a reinforced cellulose membrane.

14. The method according to claim 2 wherein the osmolyte is a polyol or poloxamer.

15. The method according to claim 2 wherein the osmolyte is a polyalkylene glycol.

16. The method according to claim 2 wherein the virus is or includes virus particles or virus like particles (VLP), and wherein the osmolyte is polyethylene glycol, whereby an amount and size of the polyethylene glycol mixed in said mixing step is dependent on a size of the virus particles or the VLP to be purified.

17. The method according to claim 1 further comprising depleting different viruses or virus and particles from the same sample based on an amount and a size of the osmolyte mixed in said mixing step.

18. The method according to claim 2 wherein the osmolyte is a polyethylene glycol of PEG-600 to PEG-10000 and/or the PEG-concentration in the sample contacted with the cellulose membrane is in the range of from 0.1 to 40% (w/w) based on the sample.

19. The method according to claim 1 wherein said cellulose membrane is a regenerated cellulose membrane or a reinforced cellulose membrane.

20. The method according to claim 1, wherein the cellulose membrane is selected from a cellulose membrane having a pore size of at least 0.8 μm.

21. The method according to claim 1, wherein the cellulose membrane is selected from a cellulose membrane having a pore size of 0.4 μm, 0.65 μm, 0.8 μm, or 1.0 μm.

22. The method according to claim 2, wherein the cellulose membrane is selected from a cellulose membrane having a pore size of at least 0.8 μm.

23. The method according to claim 2, wherein the cellulose membrane is selected from a cellulose membrane having a pore size of 0.4 μm, 0.65 μm, 0.8 μm, or 1.0 μm.

* * * * *